United States Patent
Snider

(10) Patent No.: US 8,671,770 B2
(45) Date of Patent: Mar. 18, 2014

(54) BRAZED JOINT STRAIN SHIFT DETECTION METHOD FOR MONITORING INSTRUMENT HIGH CYCLE FATIGUE LIFE

(75) Inventor: Zachary John Snider, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 384 days.

(21) Appl. No.: 12/984,358

(22) Filed: Jan. 4, 2011

(65) Prior Publication Data

US 2012/0167695 A1    Jul. 5, 2012

(51) Int. Cl.
*G01L 1/00* (2006.01)

(52) U.S. Cl.
USPC .......................................................... 73/778

(58) Field of Classification Search
USPC .......................................................... 73/778
See application file for complete search history.

(56) References Cited

U.S. PATENT DOCUMENTS

| | | | | |
|---|---|---|---|---|
| 2,821,080 A | * | 1/1958 | Gemignani | 73/827 |
| 3,845,657 A | * | 11/1974 | Hall et al. | 138/36 |
| 6,112,971 A | * | 9/2000 | Castaldo et al. | 228/126 |
| 6,191,527 B1 | * | 2/2001 | Kreider, III | 313/341 |
| 7,162,373 B1 | * | 1/2007 | Kadioglu et al. | 702/35 |
| 7,480,601 B2 | | 1/2009 | Tryon, III | |
| 7,493,809 B1 | * | 2/2009 | Ward, Jr. | 73/168 |
| 7,578,178 B2 | * | 8/2009 | Boyer et al. | 73/112.01 |
| 7,715,991 B2 | * | 5/2010 | Potdar et al. | 702/34 |
| 8,011,251 B1 | * | 9/2011 | Snider | 73/714 |
| 2004/0114665 A1 | * | 6/2004 | Park et al. | 374/179 |

OTHER PUBLICATIONS

Farrell L. Diebel, "Calculating Residual Manufacturing Stresses in Braze Joints Using ANSYS", IEEE Transactions on Electron Devices, vol. ED-34, No. 5, May 1987.*

* cited by examiner

*Primary Examiner* — Lisa Caputo
*Assistant Examiner* — Octavia Davis-Hollington
(74) *Attorney, Agent, or Firm* — Nixon & Vanderhye P.C.

(57) ABSTRACT

A method of determining when a component exceeds a predetermined stress level that is less than a fatigue failure level for the component comprising providing a braze joint in a high stress area of a target component, the braze joint designed to accommodate stress/strain up to the predetermined threshold level; measuring strain at the braze joint; observing a shift in strain indicative of a failed brazed joint; utilizing information obtained to repair, replace or set a remaining service life for the target component.

14 Claims, 4 Drawing Sheets

BRAZED JOINT STRAIN SHIFT DETECTION METHOD FOR MONITORING INSTRUMENT HIGH CYCLE FATIGUE LIFE

TECHNICAL FIELD

This invention relates to turbomachinery instrumentation and, specifically, to a technique for early detection of stress/strain in the instrumentation over a predetermined threshold level.

BACKGROUND OF THE INVENTION

Sophisticated instrumentation used to monitor operating conditions in the harsh environment of a turbomachine is complex and expensive. Undetected fatigue failure of such instrumentation can not only involve costly shutdowns for repair and/or replacement of the instrumentation, but it can also result in damage to the machine itself. For example, inlet rakes are used to monitor temperature, pressure, velocity and/or other parameters of air entering the turbine inlet and flowing across the rake. They are typically mounted to the inlet sidewall in cantilevered fashion, with the sensor beam or tube extending into the flowpath. Conditions within the flowpath can cause vibrations that may excite the natural or resonance frequency of the beam, causing catastrophic failure of the beam, which may then also result in severe damage to the downstream turbine blades or other flowpath components.

There is a need, therefore, to devise a way to monitor and detect a stress/strain level in a component (a turbine inlet rake in the exemplary embodiment) that exceeds a predetermined stress/strain level below that at which the component will fail in fatigue, thus providing the user or operator with a clear indication or early warning that the component is at risk.

BRIEF SUMMARY OF THE INVENTION

In accordance with a first exemplary but nonlimiting embodiment, there is provided a method of determining when a component exceeds a predetermined stress level that is less than a fatigue failure level for the component comprising: providing a braze joint in a high stress area of a target component, the braze joint designed to accommodate stress/strain up to the predetermined threshold level; measuring strain at the braze joint; observing a shift in strain indicative of a failed brazed joint; and utilizing information obtained in steps (b) and (c) to repair, replace or set a remaining service life for the target component.

In another exemplary but nonlimiting aspect, there is provided a method of determining when an instrumentation beam cantilevered from a casing wall at a structural joint, and subject to vibratory stress, exceeds a predetermined stress level that is less than a fatigue failure level for the instrumentation beam comprising: providing a braze joint in a high stress area of the instrumentation beam proximate the casing wall but forward of the structural joint, the braze joint designed to accommodate stress/strain up to the predetermined threshold level; measuring strain at the braze joint; observing a shift in strain indicative of a failed brazed joint; and utilizing information obtained in steps (b) and (c) to repair, replace or set a remaining service life for the instrumentation beam.

In still another exemplary but nonlimiting aspect, there is provided an inlet rake for a turbine comprising a hollow beam fitted with plural sensors, and a flange body adapted to secure the hollow beam to a turbine inlet duct; a weld joint between said hollow beam and one end of the flange body located proximate the turbine inlet duct; and a braze joint between the hollow beam and an opposite end of the flange body, forward of said weld joint.

The invention will now be described in greater detail in connection with the drawings identified below.

DETAILED DESCRIPTION OF THE INVENTION

Figure 1:
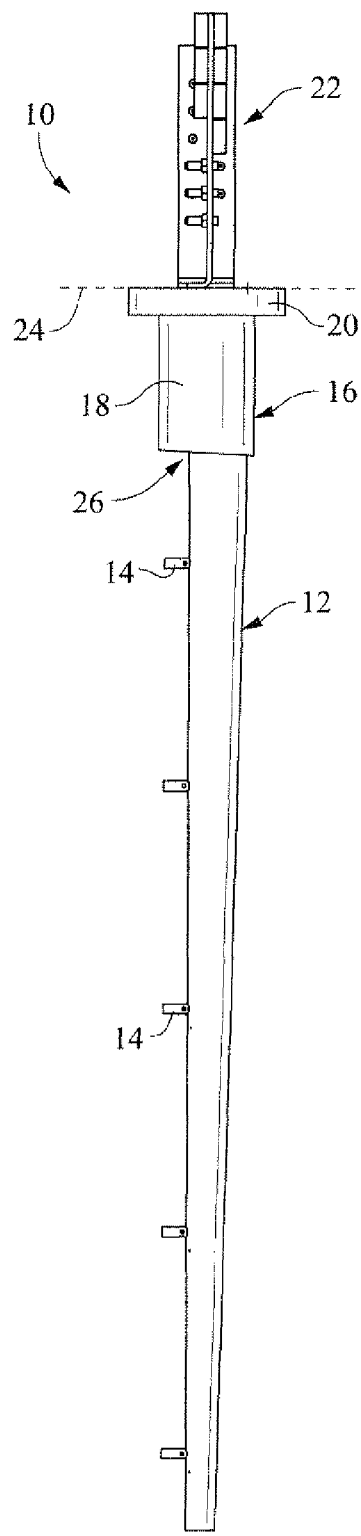
FIG. 1 is a front elevation view of a turbine inlet rake.
Figure 2:
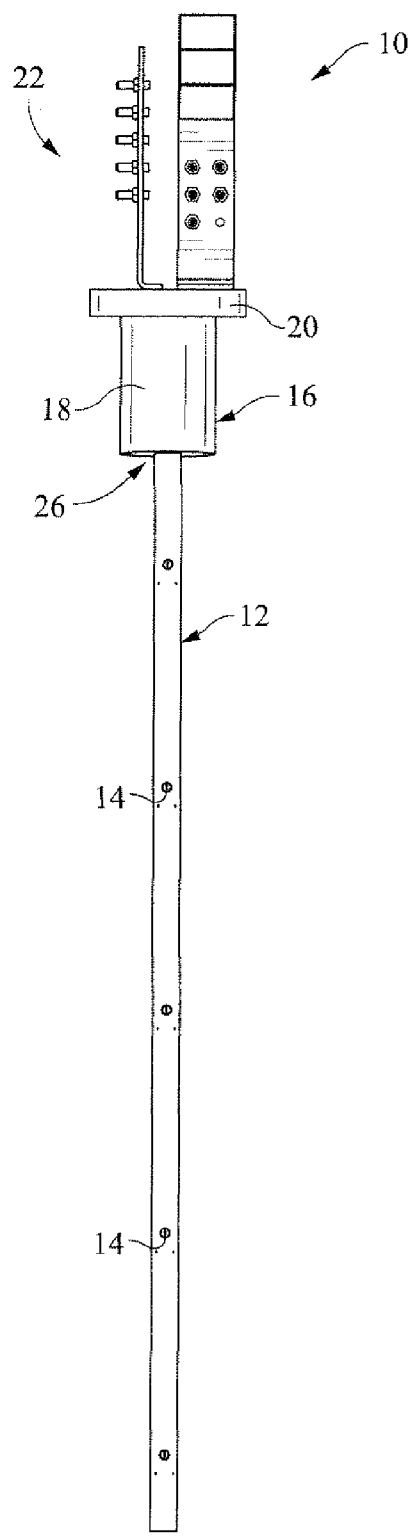
FIG. 2 is a side elevation of the rake shown in FIG. 1.

In the exemplary but nonlimiting embodiment shown in FIGS. 1-6, there is illustrated an inlet rake 10 of the type typically used to monitor various flow characteristics of air entering, for example, a turbine inlet. The inlet rake is formed as an elongated, tapered hollow body or beam 12 of generally rounded, rectangular cross-sectional shape (FIG. 4), fitted with a plurality of sensors 14 for measuring, air pressure, temperature, velocity and/or other flow parameters of air entering the turbine inlet and flowing across the rake. The inlet rake 10 mounts to a duct or casing wall (indicated at 24 in FIG. 1) at a flange body 16 that includes a cylindrical portion 18 and a radial flange portion 20. Tubes and/or sensor leads, generally indicated at 22, are fixed to the back side of the flange portion 20 which, upon installation, lies on the other side of the duct or casing wall, outside the flow path.

Figure 3:
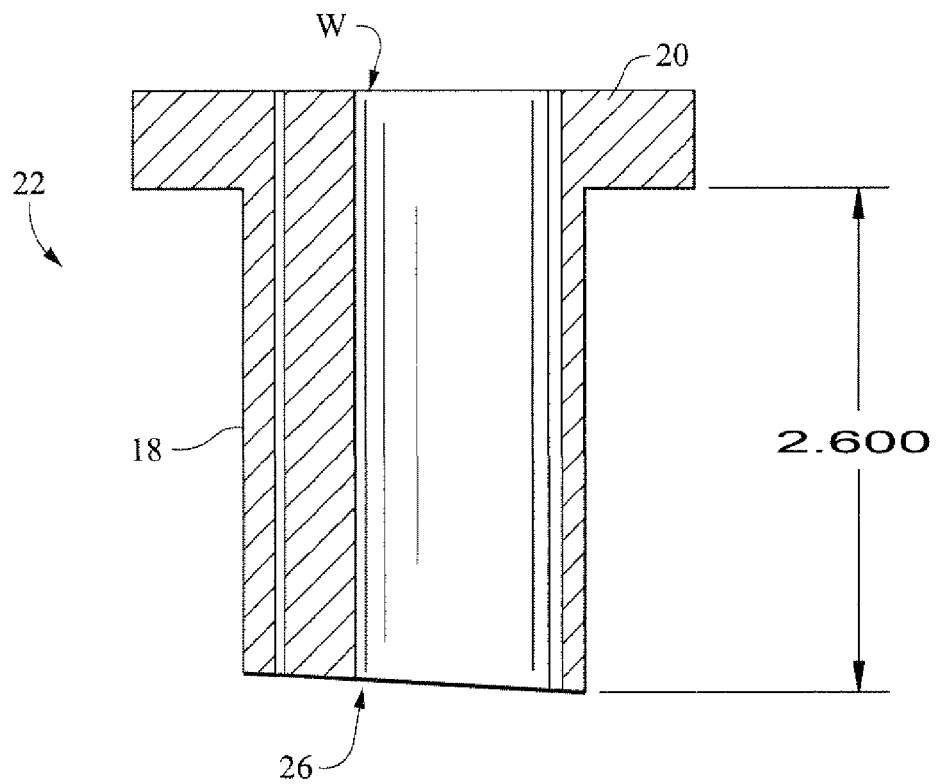
FIG. 3 is a cross section of the flange body removed from FIGS. 1 and 2 and taken along the line 3-3 of FIG. 4.
Figure 4:
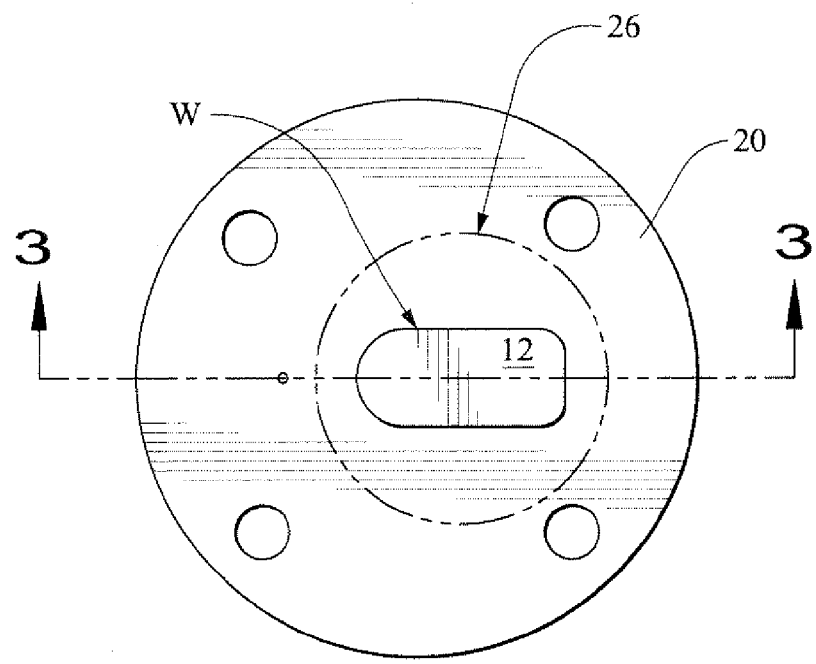
FIG. 4 is a top plan view of the flange body.

In use, the hollow body or beam 12 is essentially cantilevered from the casing wall and projecting into the air inlet flowpath, and is thus subject to high vibratory stresses, with peak stresses occurring at the flange portion 20, where the latter is bolted to the casing wall, and where the hollow body or beam 12 is welded to the flange portion (indicated at W in FIGS. 3 and 4. If the natural frequency of the hollow beam 12 is excited into resonance, the inlet rake 10 can fail at the welded joint and a separated beam 12 can also cause damage to flow path components downstream of the turbine inlet.

In an exemplary but nonlimiting embodiment, this invention provides a technique or methodology for detecting stress/strain levels in the inlet rake 10 that exceed a predetermined threshold stress level that is nevertheless below the Goodman limit of the inlet rake. The Goodman limit is material specific, and refers to the level of alternating strain the particular material can withstand for 1 million cycles before high cycle fatigue failure occurs.

Figure 6:
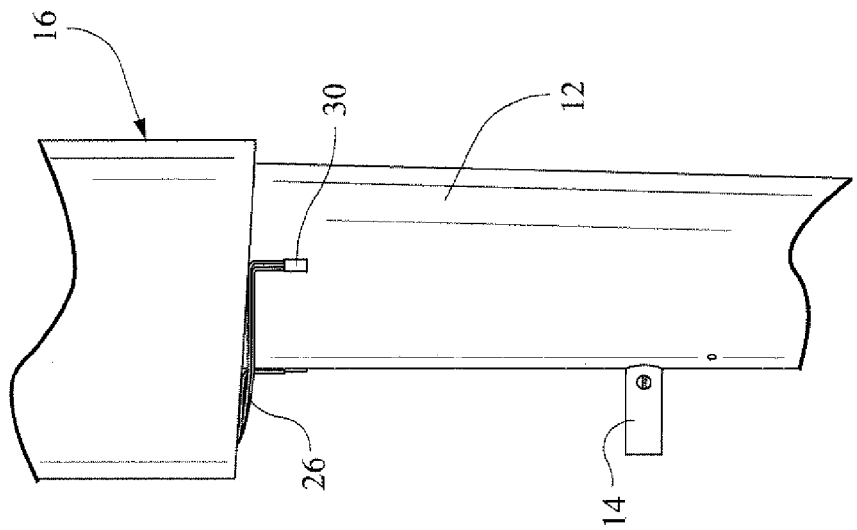
FIGS. 5 and 6 are partial elevations of the rake, showing the locations of the braze joint and strain gauges.
Figure 5:
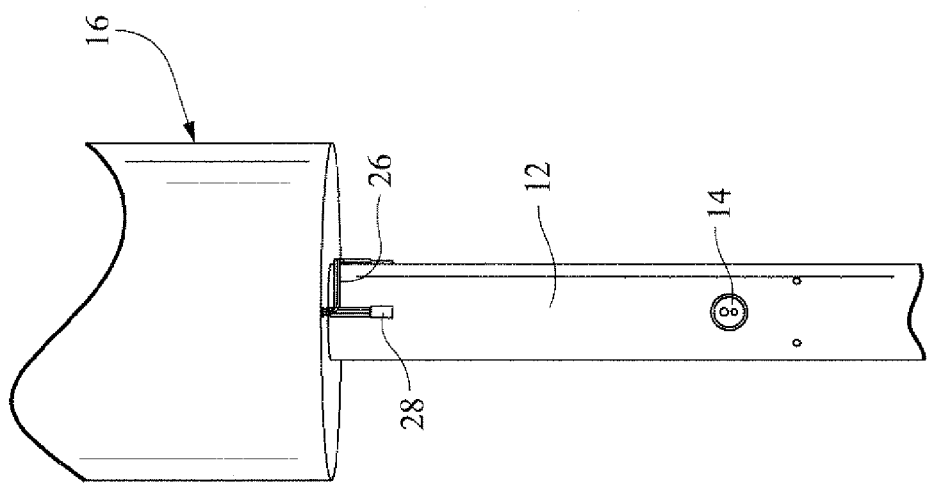

In order to implement the technique described herein, a braze joint is located at 26 (see FIGS. 1-3, 5 and 6) in an area of high stress, sized for a particular material limit. In the example embodiment, the braze joint is added where the hollow beam 12 is joined with the flange body 16, rearward of the main structural joint where the beam 12 is welded to the flange portion 20 that, in turn, is joined to the casing or duct wall 24 by bolts or other means. Since the length of the rake determines its natural frequency, the braze joint 26 effectively, albeit artificially, sets a new length for the rake in terms of establishing the natural frequency of the rake. In the exemplary embodiment, the braze joint 26 is located approximately 2.6 inches ahead of the nearest edge of the flange portion 20, as best appreciated from FIG. 3. It will be understood, however, that the exact distance is not critical and may be varied. It is important that the braze joint 26 be located closer to the free edge of the beam 12 than the weld joint. In order to monitor the strain at the braze joint, at strain gauges 28, 30 are located along the braze joint 26 with approximately a 90° spacing therebetween as best seen in FIGS. 5 and 6.

Figure 7:
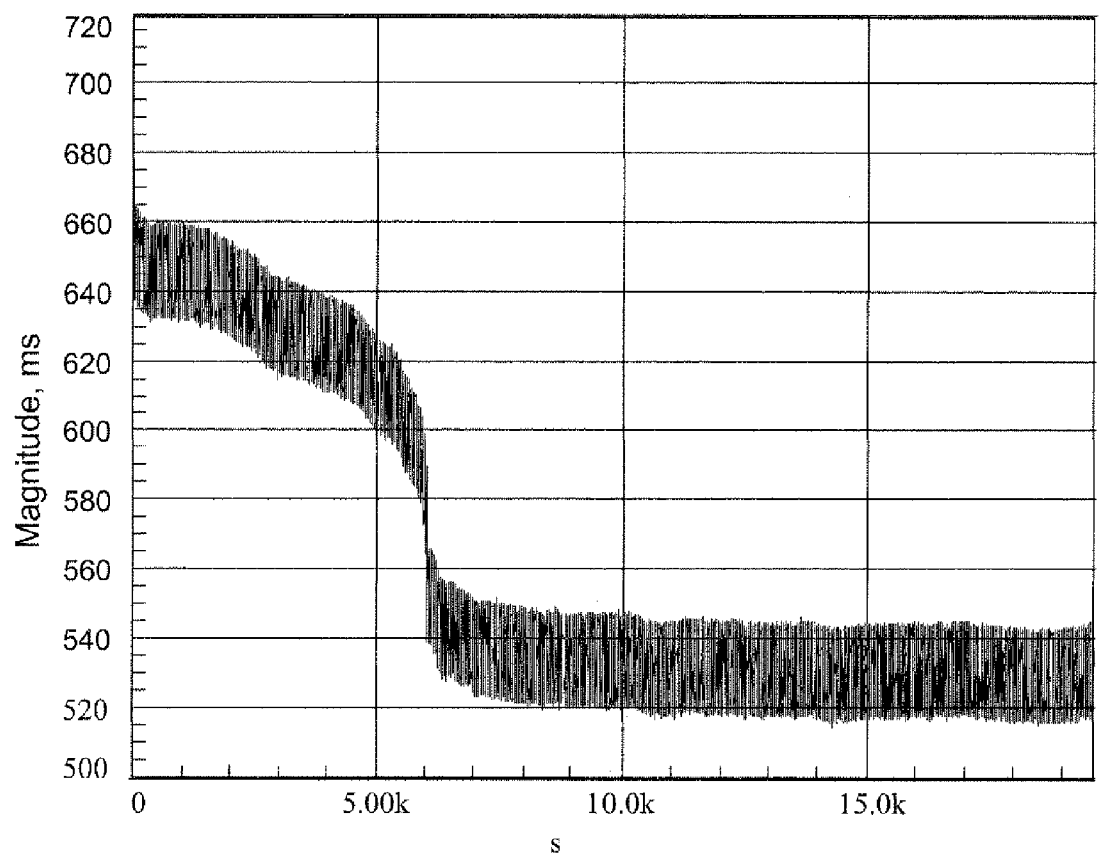
FIG. 7 is a plot of microstrains vs. time, showing a strain shift upon failure of the braze joint.

The braze joint 26 is sized to handle up to a desired predetermined stress level, preferably below the Goodman limit for the particular braze material. In the event higher than expected stress/strain levels are experienced by the braze joint, the braze joint begins to fail, causing a small crack that can be visually noted. In addition, a shift in the strain resulting from the crack can be monitored and plotted. For example, FIG. 7 shows a strain curve where strain in microstrains is plotted against time in seconds. The plot represents a beam at resonance frequency with the braze joint implemented. The curve shows a significant downward shift in strain at about 6-7 thousand seconds, indicating that the braze joint has cracked, the beam has dropped out of resonance, and that the predetermined threshold stress/strain level has been exceeded.

The failure of the braze joint 26 resets the length and thus the natural frequency of the beam 12. By bringing the beam 12 (and rake 10) out of resonance and by resetting the natural frequency, the rake is returned to an at least temporarily safe condition. The rake will then be inspected and depending on where the threshold stress/strain level has been set, repaired or replaced. It may also be possible to permit the rake to remain in use, noting the remaining cycles before the Goodman material limit of the beam is reached. Thus, early failure of the braze joint enables the operator replace, repair or set a remaining service life for the component. In other words, the disclosed detection method allows the operator to monitor the "health" of the inlet rake in a safe and reliable manner, utilizing the braze joint in the manner of a "fusible link" or "sacrificial joint". It should be noted however, that once the braze joint has failed, the rake is subject to resonant frequency failure if higher than expected strain is experienced.

While the invention has been described in connection with a turbine inlet rake, it will be appreciated that there are many other applications for the described stress/strain detection method including other instrumentation components, or even turbine components that are subject to severe vibration.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

I claim:

1. A method of determining when a target component exceeds a predetermined threshold stress level at a structural joint that is less than a fatigue failure level for structural joint comprising:
   (a) providing a sacrificial braze joint in a high stress area of the target component proximate to the structural joint, the braze joint designed to accommodate stress/strain up to the predetermined threshold stress level;
   (b) measuring strain at the sacrificial braze joint;
   (c) observing a shift in strain indicative of a failed braze joint; and
   (d) utilizing information obtained in steps (b) and (c) to repair, replace or set a remaining service life for the target component.

2. The method of claim 1 wherein the target component is cantilevered from a support wall at the structural joint subject to failure, and wherein the braze joint is located forward of the structural joint.

3. The method of claim 2 wherein step (b) is carried out using strain gauges at the braze joint.

4. The method of claim 3 wherein first and second strain gauges are located at the braze joint, spaced from each other by about 90°.

5. The method of claim 2 wherein the target component is an inlet rake for a turbine.

6. The method of claim 5 wherein the inlet rake comprises an elongated hollow beam joined to a flange body at the structural joint, and wherein step (a) is carried out by providing the braze joint at an interface between the hollow beam and the flange body, forward of the structural joint.

7. A method of determining when an instrumentation beam cantilevered from a casing wall at a structural joint, and subject to vibratory stress, exceeds a predetermined stress level that is less than a fatigue failure level for the structural joint of the instrumentation beam comprising:
   (a) providing a sacrificial braze joint in a high stress area of the instrumentation beam proximate the casing wall but forward of the structural joint, the braze joint designed to accommodate stress/strain up to the predetermined stress level;
   (b) measuring strain at the braze joint;
   (c) observing a shift in strain indicative of a failed braze joint; and
   (d) utilizing information obtained in steps (b) and (c) to repair, replace or set a remaining service life for the instrumentation beam before fatigue failure at the structural joint.

8. The method of claim 7 wherein said instrumentation beam comprises an inlet rake located in a turbine inlet flowpath, said inlet rake mounting a plurality of sensors.

9. The method of claim 8 wherein step (b) is carried out using strain gauges at the braze joint.

10. The method of claim 8 wherein first and second strain gauges are located at the braze joint, spaced from each other by about 90°.

11. An inlet rake for a turbine comprising a hollow beam fitted with plural sensors, and a flange body adapted to secure said hollow beam to a turbine inlet duct; a weld joint between said hollow beam and one end of said flange body located proximate the turbine inlet duct; and
   a sacrificial braze joint between said hollow beam and an opposite end of said flange body, forward of said weld joint, wherein said sacrificial braze joint is set to fail at a stress level lower than a Goodman limit for a braze material used to form the braze joint.

12. The inlet rake of claim 11 wherein said flange body includes a substantially cylindrical portion and a radial flange portion, said weld joint located in said radial flange portion, and said braze joint located in said substantially cylindrical portion.

13. The inlet rake of claim 12 wherein said hollow beam has a rounded rectangular cross section received in a similarly shaped bore in said flange body.

14. The inlet rake of claim 12 in combination with a turbine inlet duct wall, wherein said inlet rake is mounted to said turbine inlet duct wall via fasteners extending through said radial flange portion.

* * * * *